(12) United States Patent
Cong et al.

(10) Patent No.: US 7,728,309 B2
(45) Date of Patent: Jun. 1, 2010

(54) HIGH THROUGHPUT SCREEN METHOD AND SYSTEM

(75) Inventors: Peijun Cong, Shanghai (CN); Zhuo Wang, Shanghai (CN); Youqi Wang, Palo Alto, CA (US)

(73) Assignee: Yashentech Corporation, Shanghai (CN)

( * ) Notice: Subject to any disclaimer, the term of this patent is extended or adjusted under 35 U.S.C. 154(b) by 378 days.

(21) Appl. No.: 11/914,222

(22) PCT Filed: May 11, 2006

(86) PCT No.: PCT/CN2006/000945
§ 371 (c)(1),
(2), (4) Date: Nov. 12, 2007

(87) PCT Pub. No.: WO2006/119707
PCT Pub. Date: Nov. 16, 2006

(65) Prior Publication Data
US 2008/0191147 A1    Aug. 14, 2008

(51) Int. Cl.
    B01D 39/00    (2006.01)
    B01D 59/38    (2006.01)
    B07B 1/46    (2006.01)
    B65B 3/04    (2006.01)

(52) U.S. Cl. .......... 250/429; 250/428; 250/435; 422/68.1; 141/97; 141/286; 141/210; 204/636; 204/639

(58) Field of Classification Search .......... 250/429, 250/428, 435; 422/68.1; 141/97, 286, 210; 204/636, 639
See application file for complete search history.

(56) References Cited

U.S. PATENT DOCUMENTS

| 5,030,713 | A | 7/1991 | Wild et al. |
| 5,222,390 | A | 6/1993 | Monrabal et al. |
| 6,352,633 | B1 | 3/2002 | Liu et al. |
| 6,531,041 | B1 | 3/2003 | Cong et al. |
| 6,659,142 | B2 * | 12/2003 | Downs et al. ............ 141/9 |
| 7,037,416 | B2 * | 5/2006 | Parce et al. ............ 204/451 |

FOREIGN PATENT DOCUMENTS

| CN | 2160663 Y | 4/1994 |
| CN | 1184774 A | 6/1998 |
| CN | 1272872 A | 11/2000 |
| CN | 2476022 Y | 2/2002 |
| CN | 1451966 A | 10/2003 |
| CN | 1494655 A | 5/2004 |
| WO | WO 0210728 A | 2/2002 |

OTHER PUBLICATIONS

International Search Report for PCT/CN2006/000945 dated Aug. 31, 2006 (6 pages).

* cited by examiner

Primary Examiner—Nikita Wells

(57) ABSTRACT

The present invention discloses a high throughput screening method and system, which can be used to screen a plurality of fluid samples to ascertain their corresponding information. For example, a polymer solution sample is screened to ascertain information about its micro structure character such as including its crystallinity property. The high throughput screen system comprises a plurality of sampling passages and one or more screening devices for screening multiple samples simultaneously or almost simultaneously to get their corresponding information so as to meet research requirement of the relevant field.

9 Claims, 16 Drawing Sheets

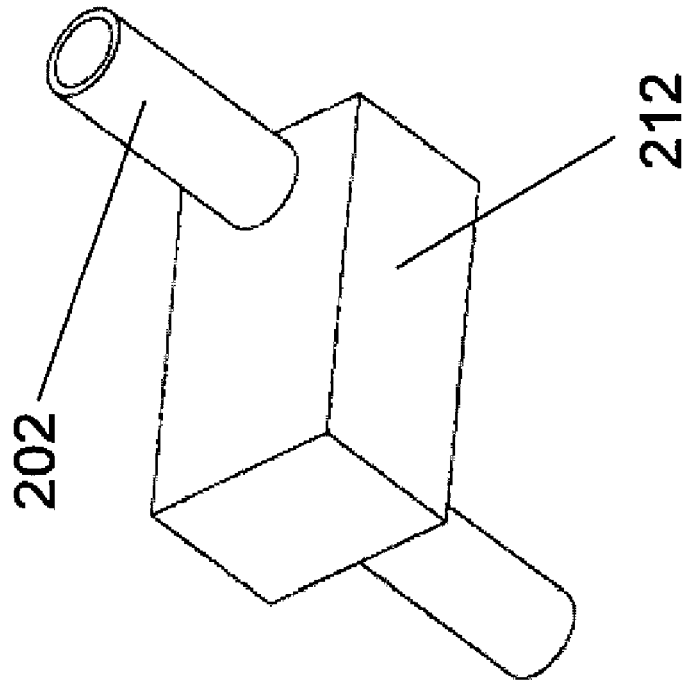
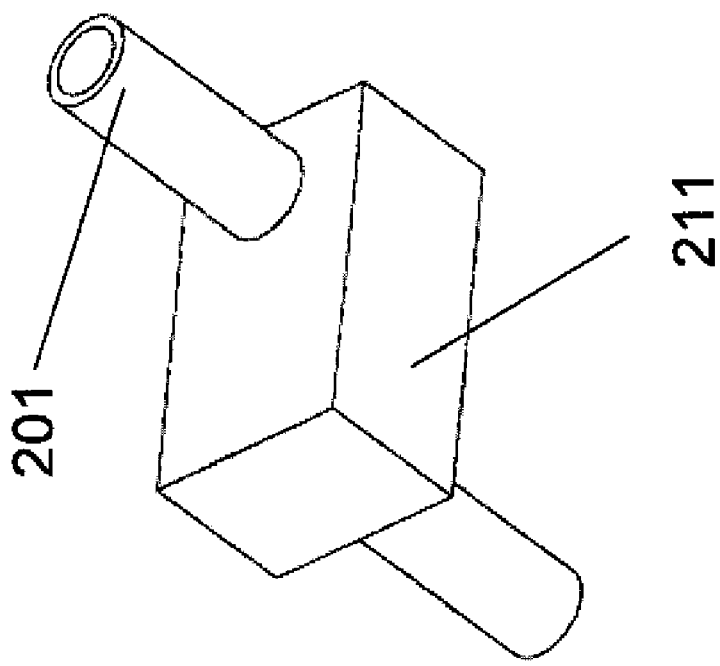
figure 2

HIGH THROUGHPUT SCREEN METHOD AND SYSTEM

FIELD

The present invention relates to a high throughput screening method and system.

BACKGROUND

Polymer microstructure characterization is the basis for developing new species and brands of polymers. At present, for a polymer such as a synthetic resin, its molecular weight, isotacticity and crystallinity are statistical average values, which can not reflect its real structure and properties information. Therefore, a correct classification method is important for microstructure research.

In polymer structure classification methods, besides the structure classification method based on relative molecular mass, the structure classification method based on degree of crystallinity has been used widely. The degree of crystallinity of the polymer is related to its chemical constituents, sequence, isotacticity distribution and branched degree, etc. and affects its mechanical property, thermodynamics property and machining property greatly. So, it is important to analyze the degree of crystallinity the polymer for the research on the polymer property and its grade.

The crystal classification method is to separate the polymer based on relationship between the crystallization of the polymer in its solution and the temperature. One is TREF (Temperature Rising Elution Fractionation), which is widely used in the polyolefin structure characterization. Recently, a new crystal classification method named as crystallization analysis fractionation (CRYSTAF) is developed, which is operated by decreasing temperature. The CRYSTAF is a one step separation method, which may need less time than a two-step separation of the TREF. So it is used widely.

Although the analyzing speed of the CRYSTAF is rapid than that of the TREF, the overall analyzing process of the CRYSTAF still needs much time such as two or more hours. So, it may slow down the development speed. In order to increase the development speed, a lot of screen devices are developed to meet the requirement for high throughput samples screen, such as including CRYSTAF 200+ of Polymer Char, which employs a selectivity valve to input a plurality of samples to the screen device in turn, and then screens the samples orderly. However, the screen device can only screen one sample one time. So, it can not meet the requirement for screening a plurality of samples simultaneously in a relatively short time. A bottleneck of the analyze speed is still existed.

Therefore, it is desired to develop a new high throughput screen method, which can screen a plurality of samples in a relatively short time to overcome drawbacks of the prior arts, The new screen method can screen the plurality of samples simultaneously or almost simultaneously. So, each sample can be screened continuously or almost continuously.

In order to match the high throughput screen method, it is also desired to develop a high throughput samples preparation method to provide the samples for screening. Thus the preparation and the screen of the samples can be accomplish continuously to improve efficiency of the polymer development and meet the requirement of the field on polymer development.

SUMMARY OF THE INVENTION

A high throughput screen method for screening a plurality of samples simultaneously or almost simultaneously, comprises two or more passages for transferring fluid samples and one or more screening device for screening the fluid samples simultaneously or almost simultaneously. The screen device can also screen each of the samples continuously or almost continuously.

Arrangement between the screen device and the passages according to different embodiments will be illustrated infra to show how to accomplish the simultaneous or almost simultaneous screen of the samples in the passages.

In one embodiment of simultaneous screen solution, the passages and the screen devices are both stationary, and the number of the screen devices are equal to or more than that of the passages. So, at least one screen device can match each of the passages. When using, all screen devices are powered simultaneously to accomplish the simultaneous screen of a plurality of fluid samples (different fluid samples are screened simultaneously). Further, each screen device can screen its corresponding fluid sample continuously (real time screen). However, if the screen device provides a discontinuous signal emission, it will be simultaneous screen for all samples but discontinuous screen for each sample. The following will illustrate the simultaneous screen solution with different embodiments.

In one embodiment of simultaneous screen solution, referring to FIG. 1, a plurality of screen devices are provided. Each screen device comprises a set of signal emitting element 111, 112 and a set of signal receiving element 121, 122, which are disposed on a base 131 and located at two opposite sides of passages 101, 102, respectively. When using, the signal emitted by the signal emitting elements 111, 112 can be transmitted by the corresponding signal receiving elements 121, 122 after passing through the passages 101, 102 and the fluid samples therein. In another embodiment, a plurality of different screen device disposed on a base can be provided according to one passage. The screen device can be any screen device known, such as including a spectrum screen device. The base can be any fixed solution known, such as including a bracket.

In another embodiment of simultaneous screen solution, referring to FIG. 2, passages 201, 202 are connected to screen devices 211, 212, so that the fluid sample flowing in the passages can be screened by the screen devices. The screen device used can be any screen device known in the art, such as including GC (Gel Permeation Chromatography)

Additionally, the embodiments shown in FIGS. 1 and 2 can be used in combinational way, and the solution can be just a combination of the two embodiments. Moreover, there is no limitation to the number and kind of the screen devices as long as the only requirement is that the screen device used can be applied to screen and get the screening data.

As to the almost simultaneous screen solution, it means the passage and/or the screen device are moveable, That is, one of the screen device and the passage are movable. That is to say, the screen device can move itself or an element of the screen device can move. For example, the screen device comprises a first independent element and a second independent element, so, movement of the screen device can be either the movement of the first independent element or the movement of the second element or the movement of the both. Thus, the almost simultaneous screen may be completed through the movement of the screen device. Additionally, there is no limitation for the number of the screen device and the passage. That is to say, the number of the screen device can be less than or equal to or more than the number of the passage. The following will illustrate the almost simultaneous screen solution with different embodiments.

In one embodiment of the almost simultaneous screen solution, referring to FIG. 3, the screen device comprises a signal emitting element 311 and a plurality of signal receiving elements 321, 322, 323. The signal emitting element 311 can make linearly forth and back movement (only show its movement tracks with broken line). A plurality of passages (no limitation to the number) is disposed between the signal emitting element and the signal receiving elements. Each passage is corresponding to the signal receiving elements 321, 322 and 323. The passage and the corresponding signal receiving elements are fixed (the fixed arrangement solution is not shown and can be any solution known). When in use, fluid samples can be introduced in the passages 301, 302, 303, and the signal emitting element 311 can move. When the signal emitting element 311 passes by the passages 301, 302, 303, the signal is emitted thereby and then received by the signal receiving element 321, 322, 323 after passing through the passages 301, 302, 303 and the fluid sample flowing therein. So, after some time, the almost simultaneous screen for all fluid samples can be accomplished. Additionally, the movement solution of the signal emitting element can be any solution known as long as the screen of all fluid samples can be accomplished in a selected period of time. For example, in another embodiment, the signal emitting element can move along a round (arc) track.

In yet another embodiment of the almost simultaneous screen solution, referring to FIG. 4, a signal receiving element 421 can move along a round track (shown in broken line), a plurality of passages 401, 402 are provided inside the track. Alternatively, the passages 401 and 402 can be disposed outside the track. Each of the passages is provided with corresponding signal emitting elements 411, 412. When in use, the fluid samples are introduced into the passages, and the signal emitting elements 411, 412 begin to emit the signals. The signal receiving element move along the track to receive the signals after the signals passed through the passage and the fluid samples therein. So, after some time, the almost simultaneous screen of all fluid samples can be accomplished. Additionally, in other embodiments, the movement solution of the signal receiving elements can be any solution known, as long as the screen of all fluid samples can be accomplished under a selected period of time. For example, in another embodiment, the signal emitting element can move along a linear track.

In yet another embodiment of almost simultaneous screen solution, referring to FIG. 5, a screen system comprises a plurality of screen devices and a plurality of passages. Each screen device comprises signal emitting elements 511, 512, and corresponding signal receiving elements 521, 522. The signal emitting elements and the signal receiving elements can move with the same angular velocity, respectively. A plurality of passages 501, 502 are disposed between the signal emitting elements 511, 512 and the signal receiving elements 521, 522. When using, the fluid samples are introduced into the passages, and the signal emitting elements and the receiving elements move together to screen all fluid samples. Alternatively, different screen device can move along different tracks.

In yet another embodiment of almost simultaneous screen solution, referring to FIG. 6, signal emitting elements 611 and 612 and signal receiving elements 621 and 622 can move in different planes, respectively. Velocity of one screen device (means the velocity of the signal emitting element and the signal receiving element) can be same as or different with the other screen device, or can be dependent on the requirement.

In the embodiments of almost simultaneous screen solution shown in FIGS. 3, 4, 5 and 6, as the screen device moves faster, the screen of different fluid samples can be more close to simultaneousness, and the screen of each fluid sample can be more close to continuousness.

Further, as to the screen of different fluid samples, the interval between the screens of two fluid samples can be different from the others, but all the intervals will seem to be almost simultaneous. The range of the "almost simultaneousness" can include 0~60 seconds, 0~50 seconds, 0~400 seconds, 0~30 seconds, 0~25 seconds, 0~20 seconds, 0~15 seconds, 0~10 seconds, 0~5 seconds, 0~3 seconds, 0~1, 0~0.5 seconds, 0~0.1 seconds, 0~0.05 seconds, 0~0.005 seconds, 0~0.0005 seconds, etc. Specially, it can be 0.0001 seconds, 0.001 seconds, 0.002 seconds, 0.01 seconds, 0.05 seconds, 0.1 seconds, 0.2 seconds, 0.5 seconds, 0.8 seconds, 1 seconds, 2 seconds, 5 seconds, 10 seconds, 15 seconds, 20 seconds, 25 seconds, 30 seconds, 35 seconds, 40 seconds, 45 seconds, 50 seconds, 55 seconds, etc. Moreover, the range of "almost simultaneousness" can also vary from 1 minute to 100 minutes. Specially, it can include 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 40 minutes, 50 minutes, 60 minutes, 80 minutes, etc.

Further, as to the screen of each fluid sample, the interval between the two screens may seem to be almost continuousness. The range of the "almost continuousness" can include 0~60 seconds, 0~50 seconds, 0~400 seconds, 0~30 seconds, 0~25 seconds, 0~20 seconds, 0~15 seconds, 0~10 seconds, 0~5 seconds, 0~3 seconds, 0~1, 0~0.5 seconds, 0~0.1 seconds, 0~0.05 seconds, 0~0.005 seconds, 0~0.0005 seconds, etc. Specially, it can be 0.0001 seconds, 0.001 seconds, 0.002 seconds, 0.01 seconds, 0.05 seconds, 0.1 seconds, 0.2 seconds, 0.5 seconds, 0.8 seconds, 1 seconds, 2 seconds, 5 seconds, 10 seconds, 15 seconds, 20 seconds, 25 seconds, 30 seconds, 35 seconds, 40 seconds, 45 seconds, 50 seconds, 55 seconds, etc. Moreover, the range of "almost continuousness" can also vary from 1 minute to 100 minutes. Specially, it can be 1 minute, 2 minutes, 3 minutes, 4 minutes, 5 minutes, 6 minutes, 7 minutes, 8 minutes, 9 minutes, 10 minutes, 13 minutes, 17 minutes, 20 minutes, 25 minutes, 30 minutes, 40 minutes, 50 minutes, 60 minutes, etc.

Additionally, the embodiments of simultaneous screen solution and the almost simultaneous screen solution can be used in combination. For example, in one embodiment, referring to FIG. 7, a screen system comprises a plurality of screen devices and a plurality of passages 701, 702. The first, second and third screen device comprise signal emitting elements 711, 712, 713 and signal receiving elements 721, 722, 723 separately. A fourth screen device 731 and a fifth screen device 732 are both single. The first screen device and second screen device can move (the movement track shown by broken line), so the first and second screen device can screen all fluid samples flowing in the passages. The third, fourth, and fifth screen devices are unmovable and can screen the corresponding fluid samples. Wherein the third and fourth screen devices both match with the same passage 701 and screen the fluid samples flowing therein. The fifth screen device is corresponding to the other passage 702 and screens the fluid sample flowing therein. Additionally, variations based on the embodiments disclosed above, are obvious to the skilled of the art.

In the embodiments of the present invention, each passage is independent to other passages during the screen process. That is to say, there is no limitation to the number of the screen devices applied to one passage. Moreover, different passages can be screened by the same/different number of screen devices. For example, in one embodiment, there are 7 screen devices and 2 passages. Wherein one passage is corresponding to 3 screen devices, the other passage is corresponding to 4 screen devices. Additionally, as to a passage corresponding to a plurality of screen devices, there is no limitation to the location relationship among the screen devices, and all the screen devices can screen the passages simultaneously or not, Further, there is no limitation to the number and kinds of the screen devices used in the screen system. If a plurality of screen devices is provided, there is also no limitation to the space relationship therebetween as long as screen device can screen the fluid sample flowing in the corresponding passage(s). For example, all screen devices are located in a plane, or different screen device locates in different plane because the passage gets a length, or the combination of the above two.

The screen device of the screen system can be any screen devices known or anticipated. Generally, there are two kinds of the screen device. The first generally comprises a signal emitting element and a signal receiving element. Signal emitted by the signal emitting element can pass through the passage and the fluid therein and be received by the signal receiving element. So, the operator can make the screen process and get the object information through reading the screen data. The second generally comprises a signal receiving element, which can receive and analyze the signal emitted from the fluid sample itself in the passage. So, the operator can make the screen process and get the object information through reading the screen data. During the screen process, each screen device is independent to other screen devices, so, the screen process of each screen device is also independent to others. Further, the number of the passage screened by different screen devices can be different. For example, a screen device can be corresponding to a passage, and it can also be corresponding to a plurality of passages and make the simultaneous screen or almost simultaneous screen. When a screen device proceeds the almost simultaneous screen to a plurality of passages, the screen interval between two passage is dependent to the screen device and the screen solution.

Specially, as to the first kind of screen device, a plurality of types of the position relationship between the signal emitting element and the signal receiving element exist. The different types of position relationships are related to the signal receiving and emitting way of the fluid sample. When the fluid sample receives the signal from the signal emitting element, it can transmit the signal in an angle according to its property. So, the signal receiving element can be angledly disposed relative to the signal emitting element according to the signal transit angle. The angle scope varies from 0 to 180 degree. Specially, it can include 30 degree, 60 degree, 90 degree, 120 degree, 150 degree and 180 degree (in this case, the signal will/can pass through the fluid sample and be received by the signal receiving element without change of spread direction. The signal emitting element and the signal receiving element will be disposed linearly). Additionally, the first kind of screen device can be any spectrum screen device known, which may comprise a radial ray source and a detector for receiving the radial. Radial rays emitted from the radial ray source can include the infrared ray, the light, the ultraviolet radiation, the X-ray and the γ-ray. Wavelength of the infrared ray is 0.75 to 1000 micron and comprises a far-infrared district with wavelength from 25 to 1000 micron, a basic frequency infrared district with wavelength from 2 to 25 micron and a near infrared district with wavelength from 0.7~2 micron. The light's wavelength is 400 to 750 nm. The ultraviolet radiation's wavelength is from 10 to 400 nm. The X-ray's wavelength is from 0.01 to 10 nm. The γ-ray's wavelength is less than 0.01 nm. Additionally, the radial ray emitted from the source can be with specifically wavelength, or a serial of wavelengths belonged to a wavelength district. Moreover, based on the screen device used, the screen solution chosen can be any solution known, such as including the ultraviolet-light screen solution, the infrared screen solution, the FTTR screen solution, the Raman screen solution. Taking the spectrum screen device as an example, the operator can operate the device according to its instruction to screen the fluid samples and get the screen data. The second kind of the screen device can be used to screen the property of the fluid sample, such as including heat capacity, electric conductivity or molecular weight. Specially, it can be calorimeter, conductivity meter, GC, etc.

When the fluid sample is screened by the spectrum screen device, the ray emitted by the radial ray source can be received by the detector after passing through the passage and the fluid in the passage In this case, Material of the passage had better be corresponding to the ray, or at least the constituent material of the portion passed by the ray can be corresponding to the ray so as to get good screen results. For example, when the ray is the ultraviolet ray source, the passage or the portion of the passage for the ray passing through is made of suitable materials, such as including quartz may be selected. When an infrared ray source is chosen to use, it had better to choose the known corresponding material for the passage or at least the portion for the infrared ray passing through, such as KBr. When a light ray source is chosen to use, it had better to choose the known corresponding material for the passage or at least the portion for passing through, such as glass, quartz.

Additionally, different portions of the passage may be made of different materials. The different portions with different materials can connect to each other directly, if possible. If not, they can connect to each other through medi-connection portions or connection devices. The medi-connection portion means that the material constituent thereof can grow together with two materials, which can not grow together. If there is no such connecting material, a connection device, such as rubber pipe or glass pipe, can be used as a medi-connection device to connect the two portions with different constituent materials so as to make a passage with different portions consisted by different materials. For example, referring to FIG. 8, a plurality of passages 800, 810, 820 are provided, and each passage is consisted of a plurality of portions with different constituent materials. The first passage 800 comprises two portions 801, 802 with different constituent materials connected to each other directly. The second passage 810 comprises two portions 811, 812 with different constituent materials connecting to each other through a medi-connection portion 813. The third passage 820 comprises two portions 821, 822 with different constituent materials connecting to each other through a medi-connection device 823. Moreover, there is no limitation to the number and relationship to the passages provided in the screen system. For example, the number can be 2, 3, 4, 5, 6, 7, 8, 9, 10, 12, 15, 17, 19, 20, 30, 50, 70, 90, 100, 200, 300, 1000, 3000, 5000, 10000, etc. The relationship of the passages can be independent to each other; or related to each other. For example, a plurality of passages are all connect to a device, such as distribution device, so all the passages have the same input source.

In one embodiment of the screen system with the spectrum screen device, please refer to FIG. 9, a plurality of passages 900, 910 are provided, and each passage comprises a plurality of portions 901, 902, 911, 912 with different constituent materials, which connect to each other directly. The constituent material for each portion is corresponding to the radial ray from the ray source 931, 932. The ray will pass through the corresponding portions, and then be received by the detector 941, 942, so as to realize the screen of the fluid samples flowing in the passages. Moreover, in other embodiments, the connection way of different portions of the passage can be any connection way disclosed above. And the relationship between the passage and the spectrum screen device can be the fixed solution or movable solution or the combination of the both, which is disclosed above.

In another embodiment of the screen system with the spectrum screen device, referring to FIG. 10, a passage 140 is divided into two sub-passages 141, 142 through a distribution device 150. The sub-passages are respectively constituent with quartz and KBr so as to respectively corresponding to the ultraviolet ray with predefined wavelength and infrared with predefined wavelength from the respective radial ray sources 161, 162 of the screen devices. The radial ray will pass through the sub-passages, and then be received by respectively corresponding detectors 171, 172, so as to realize the screen of the fluid sample. Moreover, in other embodiments, there is no limitation to the number of the sub-passages from a passage, and the number can depend to requirement. When screening, each sub-passage is independent to other sub-passages, and the constituent material for the sub-passage and the corresponding screen device can also be set according to requirement.

Further, the embodiments disclosed in FIGS. 9 and 10 can be used in a combinational way. For example, a plurality of passages is relatively disposed though a distribution. Each passage comprises a plurality of portions each consisted by different materials. The embodiment will not illustrate, since it is just the combination of the embodiments disclosed with reference to FIGS. 9, 10.

Further, all embodiments disclosed above can be used in combination. For example, in one embodiment of the combination, a plurality of passages 220, 231, 232 is provided. The first passage 220 comprises a plurality of portions 221, 222, 223 each consisted by different materials. The second and third passages 231, 232 are consisted by different materials and are disposed relatively through a distribution 230. A plurality of screen devices is provided. The first, second and third screen devices comprise signal emitting elements 241, 242, 243 and signal receiving elements 251, 252, 253, respectively. The first and second screen devices are movable (the movement track shown by the broken line), and the third screen device is stationary with respect to the first passage 220. The fourth and fifth screen devices 261, 262 respectively connect to the corresponding passages 220, 231. When screening, the first and second screen devices will screen all the fluid samples of all passages almost simultaneously. The third, fourth and fifth screen devices will only screen the fluid samples in corresponding passages.

Further, the fluid sample screened by the screen system in accordance with the present invention can selected from gaseous samples, liquid samples and solution samples. The solution sample can include a polymer solution sample. The polymer can include linear polymer of nucleic acids, cyclic polymer of nucleic acids, polysaccharide, phospholipid, polypeptide, heteropolymer, polynucleotide, polyurethane, polyester, polycarbonate, polyureas, polyamide, polyethyleneimine, polyarylene sulfide, polysiloxane, polyimide, polyacetate, olefin polymer and olefin copolymer, etc. The olefin polymer can include polythene, polypropylene, polybutylene, polyamylene, polyhexene, polyheptylene and polyoctene, etc. Olefin copolymer can selected from all kinds of copolymers of the olefin disclosed above, such as ethylenepropylene copolymer, ethylenebutylene copolymer. Through screening the polymer solution, the information, such as including the crystalline of the polymer therein can be gotten. Further, when the polymer solution sample is introduced to the passage, the situation on its structure and concentration will selected from the following four special situations: the first is that the structure and the concentration remains unchangeably, the second is that the structure remains unchangeably, but the concentration change dynamically, the third is that the structure change dynamically, but the concentration remains unchangeably, the fourth is that the structure and the concentration change dynamically. Taking the fourth situation as an example, it means that the polymer structure and the concentration of the polymer sample solution change dynamically with time. That is to say, take a spectrum screen device as an example, each time the polymer sample in the solution passed through by radial ray emitted by the radial ray source is different from the polymer sample of next time.

Further, the screen system in accordance with one embodiment of the present invention can connect to a high throughput solution samples preparation system so as to accomplish the preparation and screen of samples continually.

Additionally, the present invention provides a high throughput solution samples preparation system. Referring to FIG. 12, the solution samples preparation system comprises a liquids distributor 1, a plurality of first vessels 2, vibrate heating platform 3, a plurality of second vessels 4 and a temperature control chamber 5. When in use, the solvents are distributed to the first vessels with the samples therein by the liquid distributor so as to get primary solution samples. The vibrate heating platform will vibrate and heat the first vessels, so as to make the sample dissolve well in the solvent and to obtain solution sample with good quality. When the primary solution samples are ready, they will be introduced into the corresponding second vessels. Then the second vessels will be put into the temperature control chamber 5, and the final solution sample is made the temperature of the chamber is controlled. Finally, the final solution sample will be discharged, and the preparation of the solution sample is accomplished. Moreover, the high throughput solution sample preparation system further comprises an electrical balancer 6 and a base 7 for arranging the first vessels. Moreover, the high throughput solution sample preparation system further comprises a plurality of third vessels each connecting to a second vessel so that the liquid in the third vessel can be introduced into the second vessel. Additionally, The first vessel, second and third vessel used can be any vessels known with storage function, such as cuvette, column, etc.

The high throughput solution sample preparation system and high throughput screen system may be connected to each other through connection between the second vessel and the passage. So, the solution sample can flow into the passage from the second vessel to be screened. The flowing way of the fluids in the system can be any flowing way known, such as a way powered by a pump, or a way powered by pressure, or a way powered by vacuum, or a way powered by gravity itself, etc. In an embodiment of the connection solution between the high throughput solution sample preparation system and the high throughput screen system, please referring to FIG. 13, the high throughput solution sample preparation system comprises a second vessel 4 and a third vessel 8 and the high throughput screen system defines a passage 9. The third vessel connects to the second vessel with a mass flow controller (MFC) 10 arranged therebetween, and the second vessel connects to the passage with a filter 11 arranged therebetween. The arrangement of the MFC and the filter is for getting better result of the preparation and the later screen of solution sample. In other embodiments, they can be not included. Moreover, the whole system can be operated by automatic technique known.

Further, in another aspect, the present invention provides a temperature control chamber, which can be used in the high throughput solution sample preparation system in accordance with one embodiment of the present invention. In an embodiment, referring to FIGS. 14 and 15, a temperature control chamber 20 has an inner surface 21 and an outer surface 22. The inner surface 21 may enclose a cavity. An inner temperature control element 23 is disposed on the inner surface 21. An outer temperature control element 24 is disposed on the outer surface 22. An insulator 25 is disposed between the inner surface 21 and the outer surface 22. In the current embodiment, the temperature change between the inner surface 21 and the outer surface 22 is minimized to reduce the rate of heat loss/gain to or from the inside of the chamber 20. The insulator 25 may be any insulating material, vacuum, or combination thereof. Optionally, one or more reflective shields may be present between the inner surface 21 and the outer surface 22 of the chamber 20 to minimize heat loss through radiation.

In yet another embodiment, the present invention provides a high throughput screen method, which comprises steps of:

firstly, introducing two or more fluid samples into the respective passages, which can be screened by one or more screen devices;

secondly, causing the screen devices simultaneously or almost simultaneously to screen all fluid samples in the passages.

The simultaneous screen solution means that the screen devices have a fixed position to the corresponding passages, and the number of the screen devices is more than the number of the passages. So, each fluid sample can be screened by one or more screen devices. The embodiments of the simultaneous screen solution can refer to the disclosure disclosed above. The almost simultaneous screen solution means the position relationship between the screen device and the passage is unfixed, or at least the element of the screen device has an unfixed position relationship with the passage. In this case, there is no limitation to the number relationship between the screen devices and the passages. Through the rapid movement of the screen device or its element, the almost simultaneous screen solution can be made. The embodiments of the almost simultaneous solution can refer to the disclosure disclosed above. Moreover, the two screen solution can be used in combination, and the embodiments can refer to the disclosure disclosed above.

Moreover, the high throughput screen method can be also combined with the high throughput solution sample preparation method. So, the preparation and the screen of the solution sample can be accomplished continually.

In yet another embodiment, the invention provides a high through solution samples preparation method, which can be a high throughput temperature rising elution fractionation, or a high throughput crystallization analysis fractionation.

Compared to the traditional temperature rising elution fractionation, the high throughput temperature rising elution fractionation means that a plurality of solution samples can be prepared in parallel. It comprises the following steps: firstly, dissolving a plurality of samples into respective corresponding solvents to get the solution samples, which stored in respective corresponding vessels; secondly, putting the vessels in a temperature control chamber, and then decreasing the environmental temperature. With the descent of the temperature, crystal will separate out in each solution sample; thirdly, rising the temperature when the temperature degree meet the predefined degree, and introducing corresponding washing solvent into each vessel, and beginning to output the solution samples at the same time. Additionally, the high throughput temperature rising elution fractionation may be combined with the high throughput screen method in accordance with the present invention by just connecting the vessels to the passages. Therefore, the solution samples discharged from the vessels will flow into the passage directly, and then be screened.

There is no difference in the treatment for each solution sample. For example, the vessels can be filled with fillers, which are used as the crystal seeds. The fillers can be made of glass, quartz, inorganic materials, or polymer heating resistant materials, etc. Moreover, in the second step, the begin-point and the end-point of the temperature are dependent to the requirement, and so do the taken time and the velocity of the temperature adjusting. The temperature can vary from $-190°$ C. to $400°$ C., or from $-150°$ C. to $350°$ C., or from $-100°$ C. to $350°$ C., or from $-50°$ C. to $250°$ C., or from $-40°$ C. to $200°$ C., or from $-20°$ C. to $160°$ C. The take time may not be limited and related to practical requirement. For example, the taken time for the temperature adjusting can vary from 0 to 72 hours, or from 1 to 48 hours, or from 2 to 24 hours. Specially, it can be 48 hours, 36 hours, 24 hours, 20 hours, 18 hours, 15 hours, 12 hours, 10 hours, 9 hours, 8 hours, 6 hours, 5 hours, 4 hours, 3 hours, 2 hours, 1 hours, etc. There is also no limitation to the range for the velocity of the temperature adjusting, and it also depends on the requirement. For example, the range of the velocity of the temperature adjusting can vary from $0.001°$ C./min to $10°$ C./min, or from $0.01°$ C./min to $5°$ C./min, or from $0.1°$ C./min to $2°$ C./min. specially, it can be $0.01°$ C./min, $0.03°$ C./min, $0.05°$ C./min, $0.07°$ C./min, $0.09°$ C./min, $0.1°$ C./min, $0.2°$ C./min, $0.3°$ C./min, $0.4°$ C./min, $0.5°$ C./min, $0.6°$ C./min, $0.7°$ C./min, $0.8°$ C./min, $1°$ C./min, $2°$ C./min, $3°$ C./min, $4°$ C./min, $5°$ C./min, $6°$ C./min, $7°$ C./min, $8°$ C./min, $9°$ C./min, etc. Specially, in one embodiment, there is a temperature descent process, which may take 3 hours to descent from $150°$ C. to $42°$ C. The velocity in each hour is respectively $0.5°$ C./min, $0.6°$ C./min and $0.7°$ C./min. In another embodiment, there is a temperature descent process, which may take 5 hours to descent from $150°$ C. to $30°$ C. The velocity is $0.4°$ C./min. Moreover, as to each solution sample, the solvent used in the first step can be same as or different from the washing solvent used in the third step. If they are different, they may have similar property, such as including both being benzene kinds solvents so as to get better solution samples.

Compared to the traditional crystallization analysis fractionation, the high throughput crystallization analysis fractionation means that a plurality of solution samples can be prepared in parallel, and there is no difference in the preparation for each solution sample. It comprises the following steps, firstly, dissolving the samples in the corresponding solvents provided in the vessels; secondly, putting the vessels with the solutions therein into a temperature controlled environment, and then decreasing the temperature while outputting the solution samples from the vessels at the same time. Additionally, the high throughput crystallization analysis fractionation can be combined with the high throughput screen method just by connecting the vessels to the passages.

Therefore the solution samples output from the vessels will flow into the passage directly, and so begins the screening of the solution samples.

Further, as to the two high throughput solution samples preparation methods disclosed above, the solution samples can firstly pass through a filter before it enter into the passage so as to avoid crystal sample in the solution to enter into the passage. As to the arrangement of the filter, it can be disposed in at least one of the vessel and the passage. The arrangement way of filter and itself will not be explained in detail, as they are the known technology in the art.

Further, as to the two high throughput solution samples preparation methods disclosed above, the temperature for preparation and the temperature for the screening can change synchronously or not. The synchronous change of the temperature means that the two temperatures are the same degree at the same time. For example, the temperature of the solution sample is 60° C. when it flows into the passage. The temperature is also 60° C. when it is screened by the radial source. Alternatively, the asynchronous change of the temperature means that the two temperatures are different at the same time, for example, the temperature of the solution sample at screening is higher than the temperature of the solution sample at preparation. For example, the temperature of the solution sample is 60° C. when it flows into the passage, and the temperature is 65° C. when it is screened by the radial source. The setting of the temperatures can depend on the requirement of the operator.

Additionally, as to the two high throughput solution samples preparation methods disclosed above, methods for the solution sample entering from the vessel to the passage and the washing solvent entering into the vessel in the third step of the high throughput temperature rising elution fractionation can be any way known by the art, such as a way powered by a pump, or a way powered by pressure, or a way powered by vacuum, or a way powered by siphon, or a way powered by gravity itself, etc.

Further, the high throughput screen method of the present invention can cooperate with the high throughput data process method so as to accomplish the screen and data process continually and get the information, which can not get from the screen device directly. Moreover, the data process solution can be a method according to Lambert-Beer's Law, or proportion method. Further, the internal standard method can be used in the data process.

Compared to the traditional screen method for screening a single sample, the high throughput screen method in accordance with the embodiments of the present invention can accomplish a plurality of samples screen in a short time, and meet the development requirement of the field. Moreover, the high throughput sample preparation method can cooperate with the high throughput screen method in accordance with the embodiments of the present invention so as to accomplish the high throughput sample preparation and screen continually. Thus, increasing the development efficiency of the field.

BRIEF DESCRIPTION OF THE DRAWINGS

FIG. 2 is a schematic diagram of the high throughput screen system in accordance with another embodiment of the present invention, which can screen a plurality of samples simultaneously;

DETAILED DESCRIPTION OF THE PREFERRED EMBODIMENTS

Figure 1:
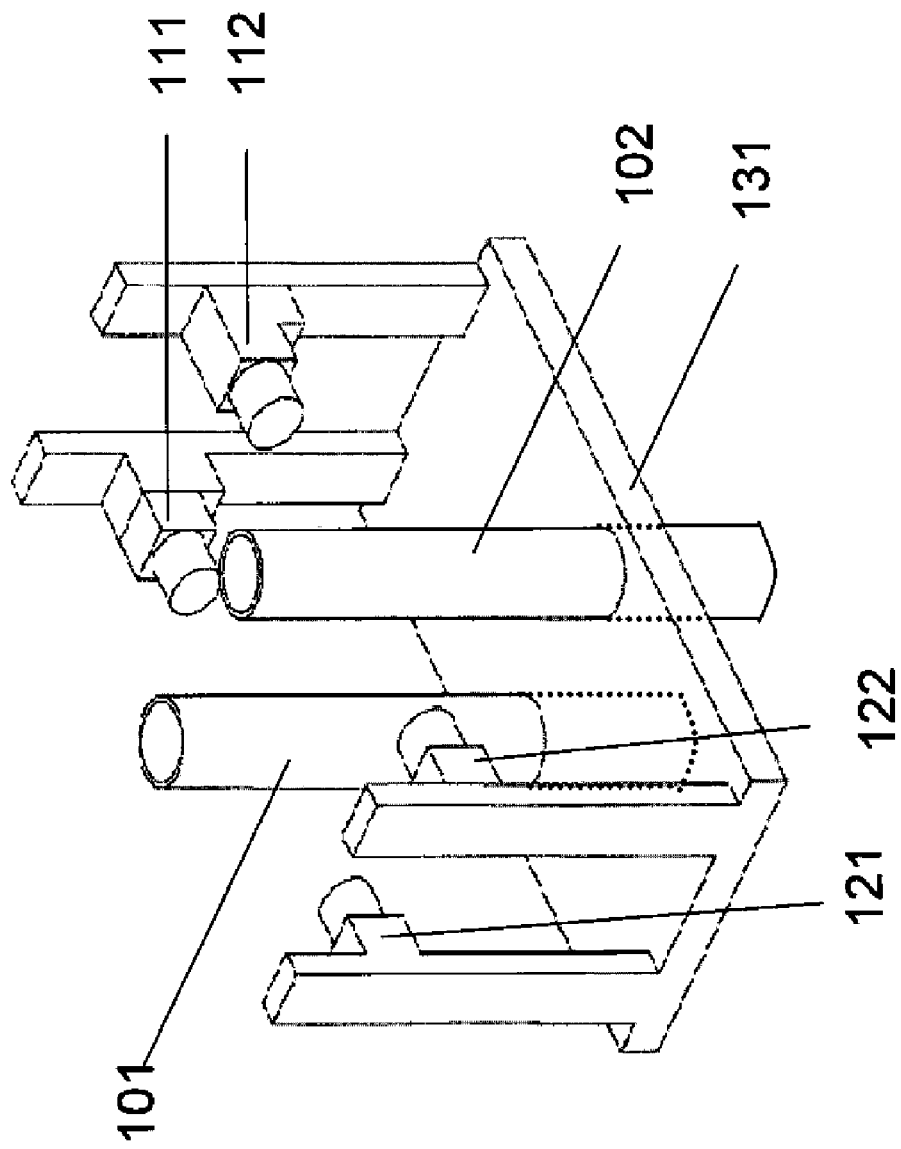
FIG. 1 is a schematic diagram of the high throughput screen system in accordance with one embodiment of the present invention, which can screen a plurality of samples simultaneously.
Figure 3:
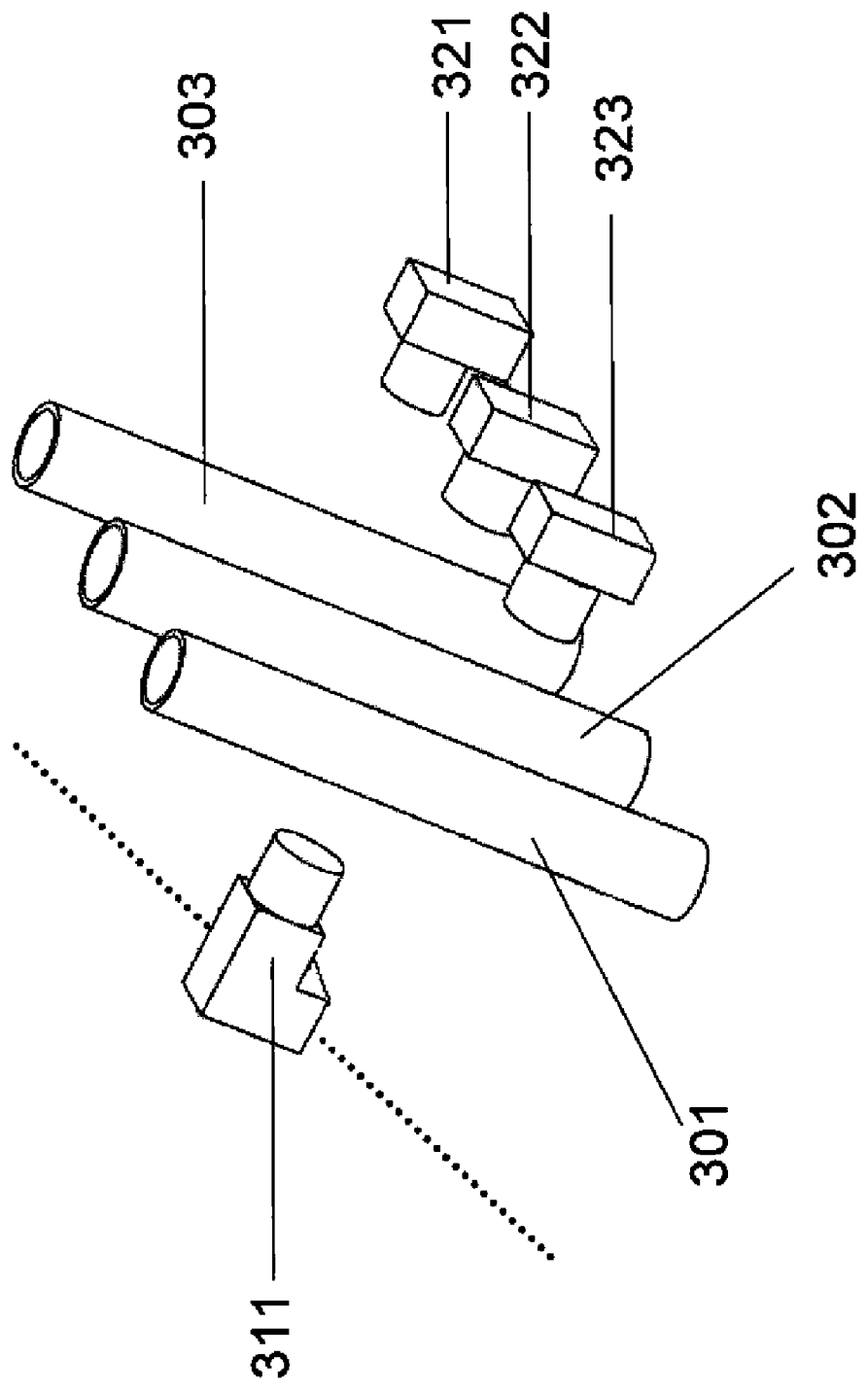
FIG. 3 is a schematic diagram of the high throughput screen system in accordance with yet another embodiment of the present invention, which can screen a plurality of samples almost simultaneously.
Figure 4:
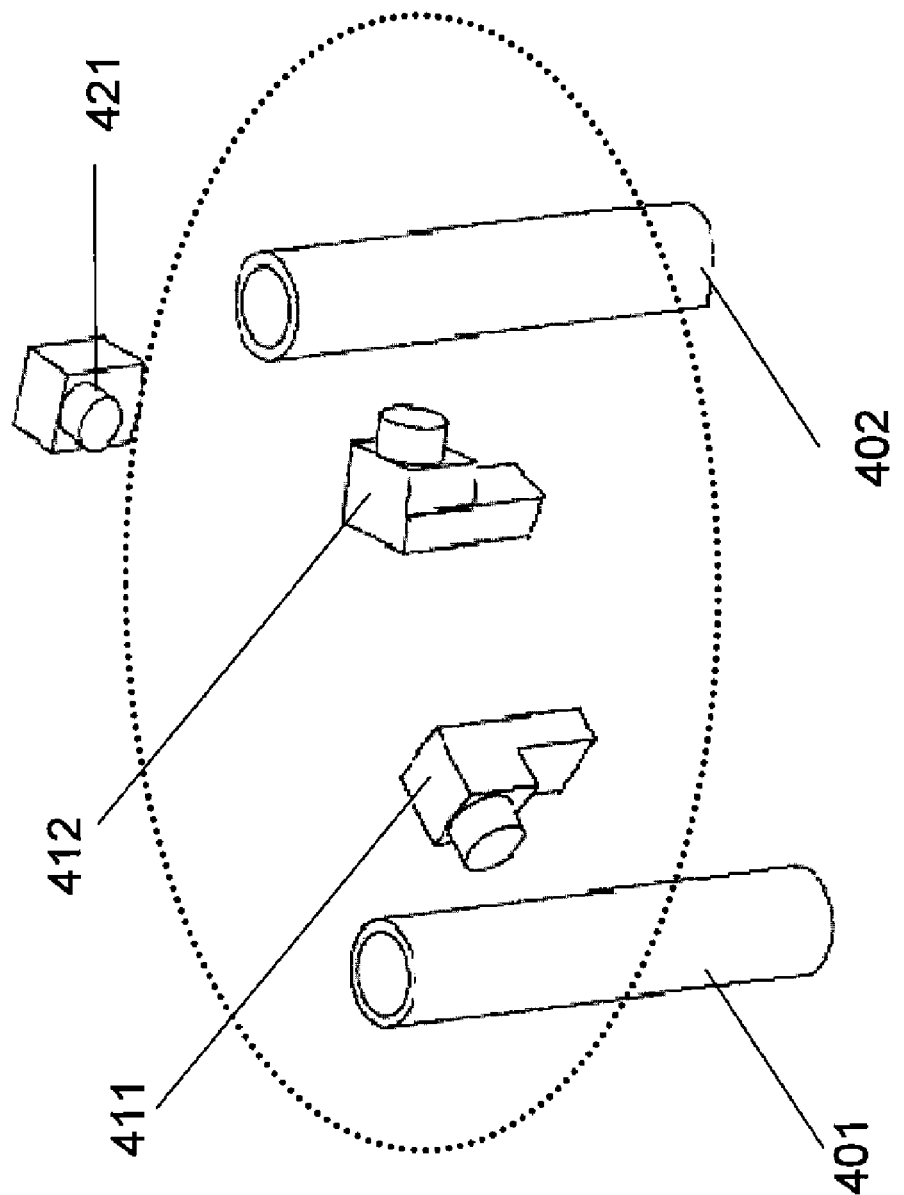
FIG. 4 is a schematic diagram of the high throughput screen system in accordance with of yet another embodiment of the present invention, which can screen a plurality of samples almost simultaneously.
Figure 5:
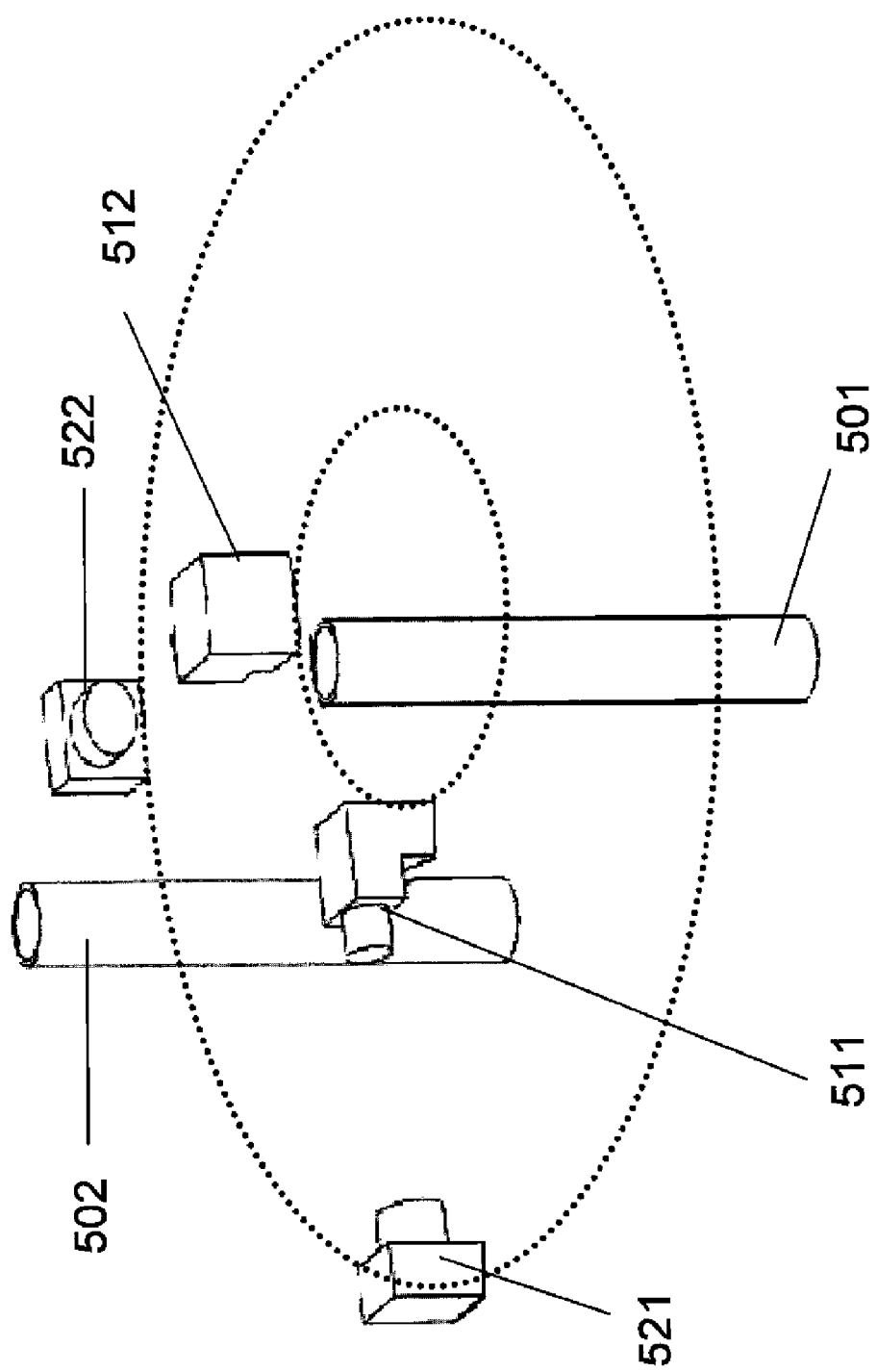
FIG. 5 is a schematic diagram of the high throughput screen system in accordance of yet another embodiment of the present invention, which can screen a plurality of samples almost simultaneously.
Figure 6:
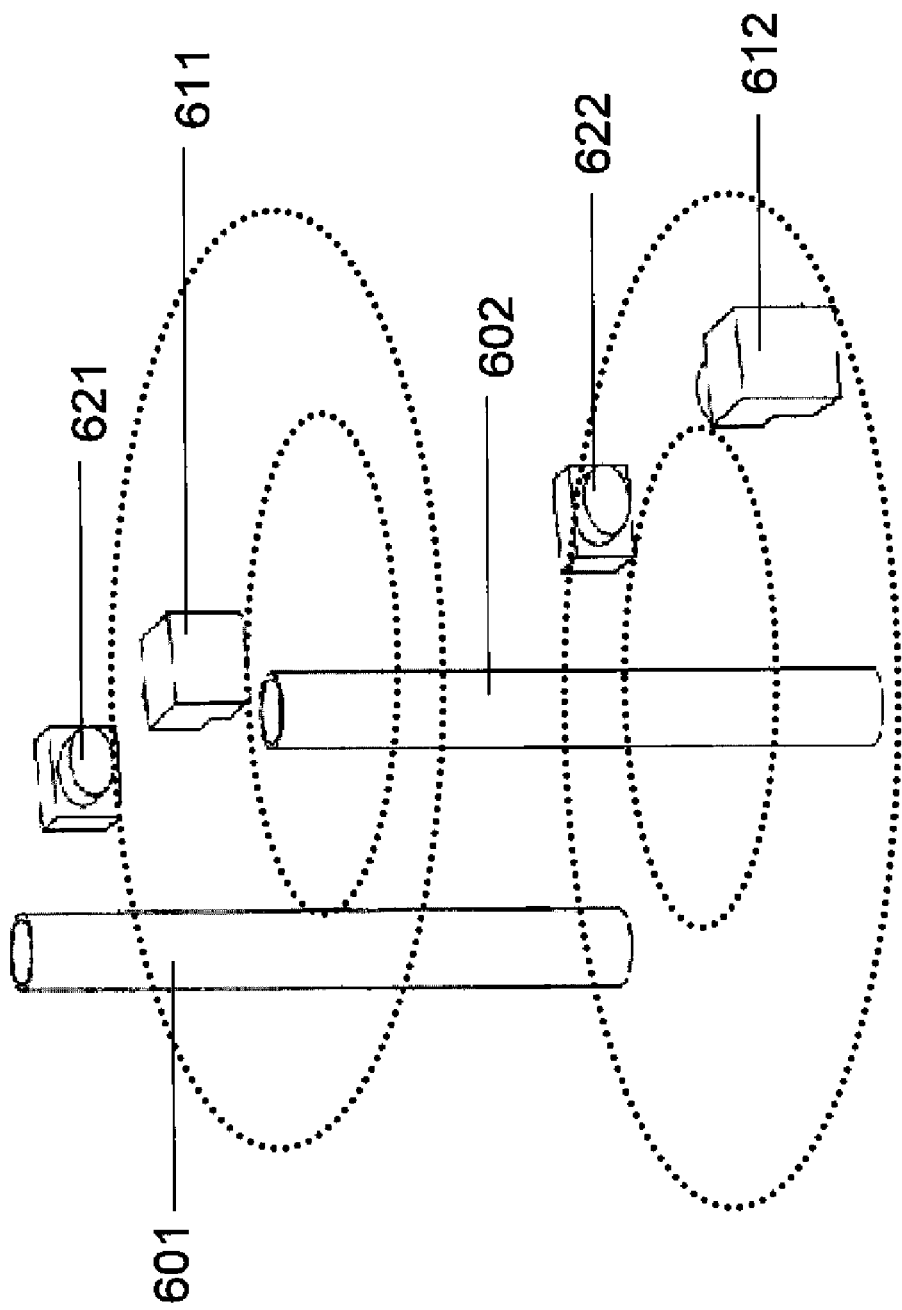
FIG. 6 is a schematic diagram of the high throughput screen system in accordance with yet another embodiment of the present invention, which can screen a plurality of samples almost simultaneously.
Figure 7:
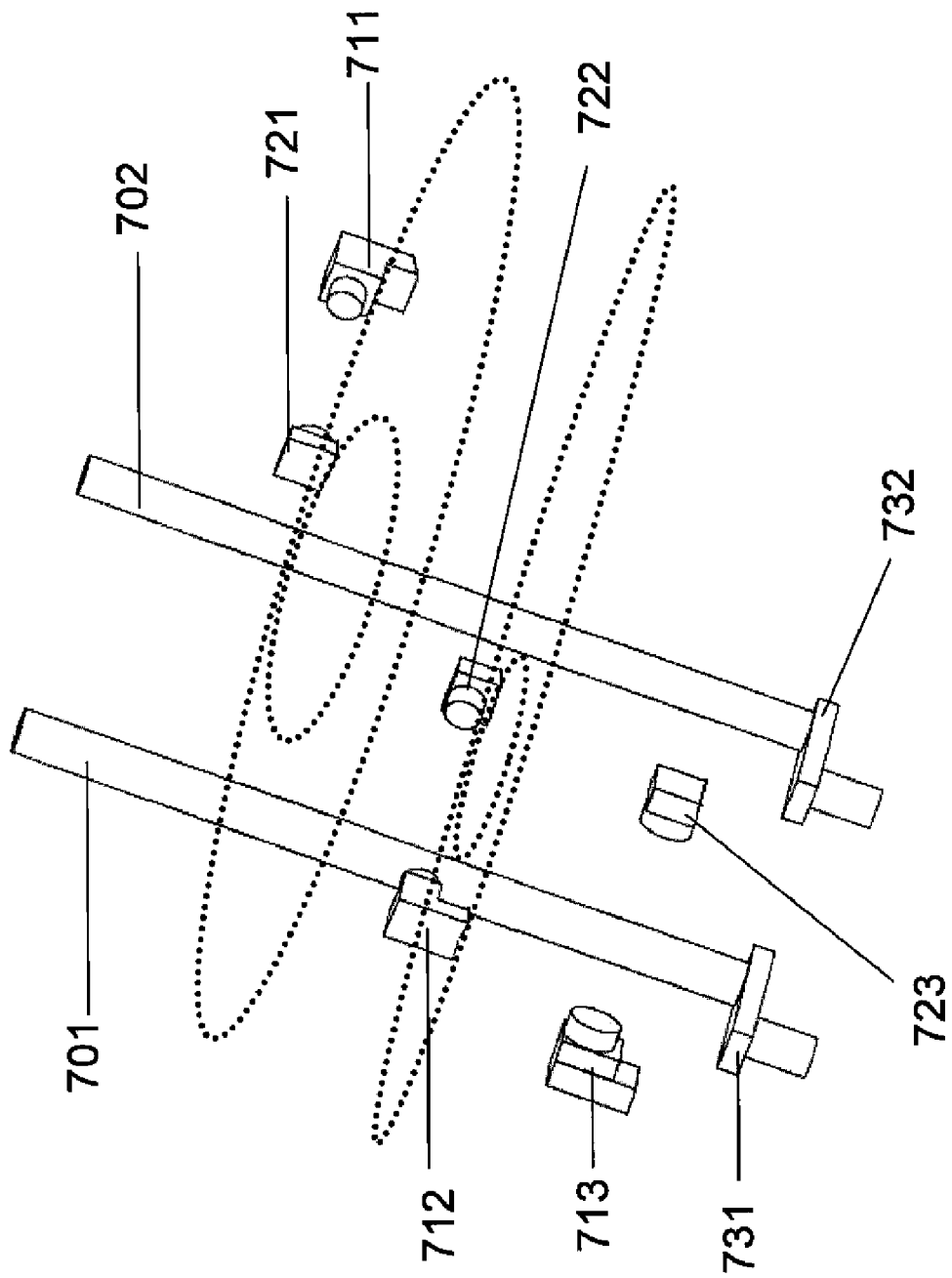
FIG. 7 is a schematic diagram of the high throughput screen system in accordance with yet another embodiment of the present invention.
Figure 8:
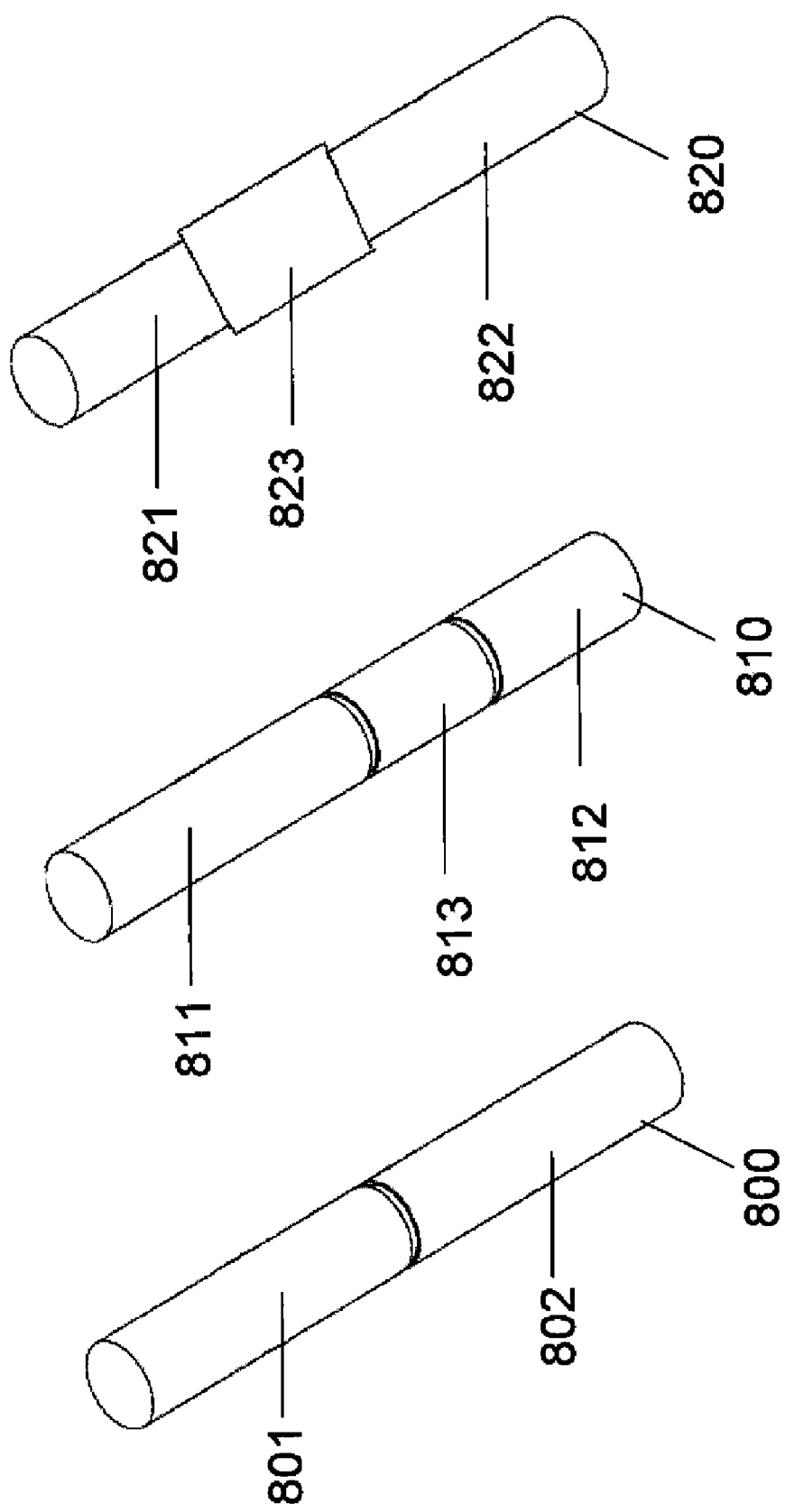
FIG. 8 is a schematic diagram of the passages of the high throughput screen system in accordance with one embodiment of the present invention.
Figure 9:
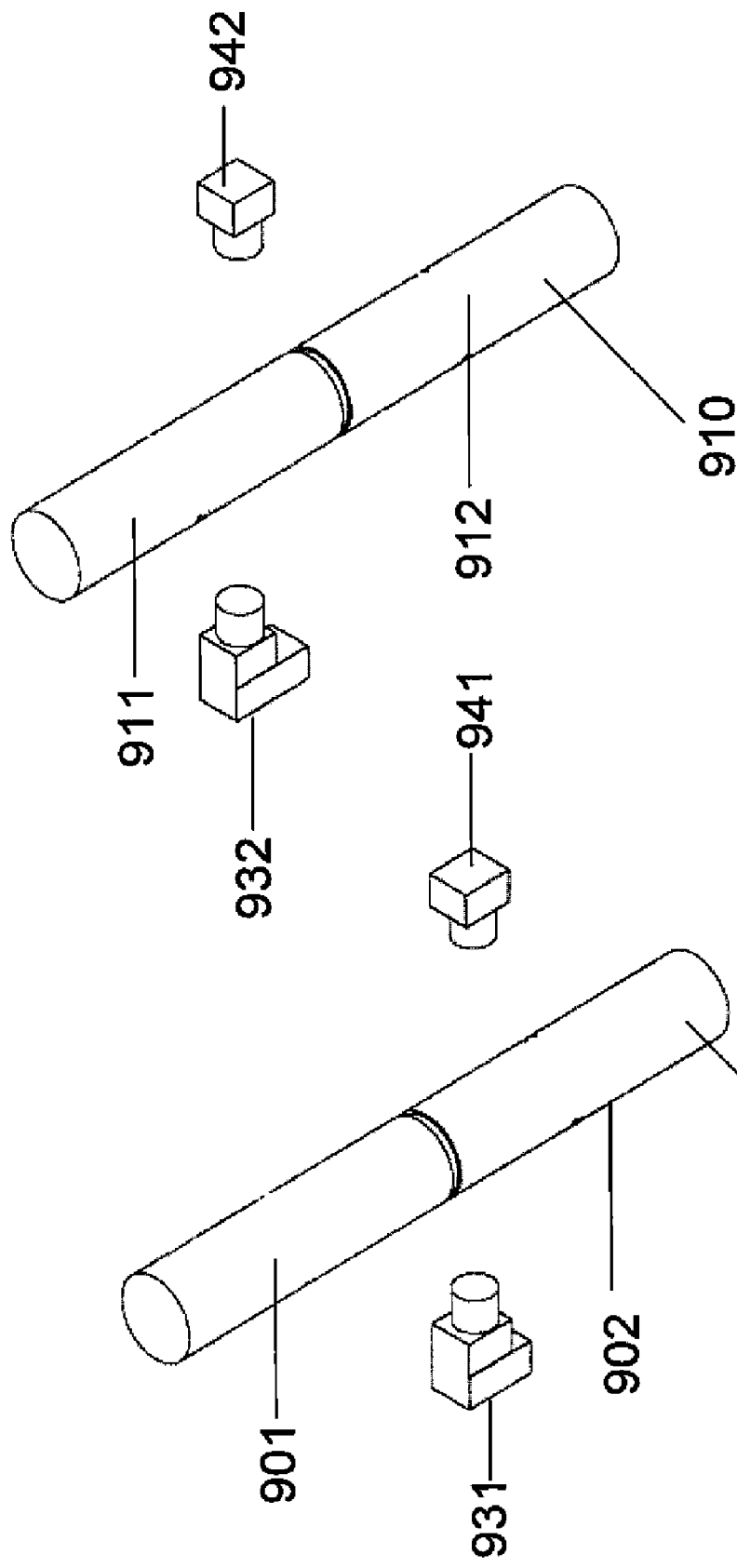
FIG. 9 is a schematic diagram of the high throughput screen system in accordance with yet another embodiment of the present invention, which employs spectrum screen devices.
Figure 10:
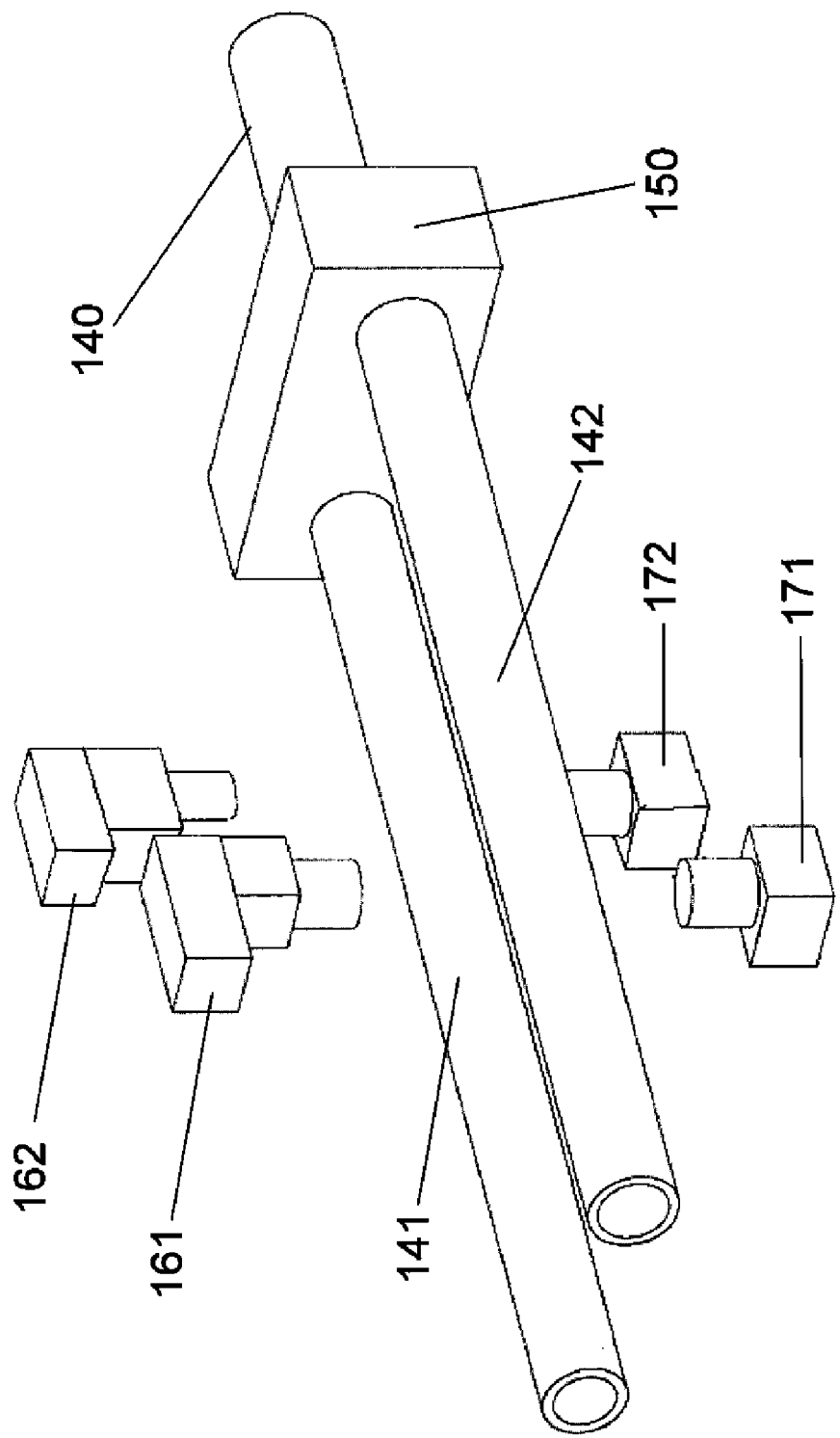
FIG. 10 is a schematic diagram of the high throughput screen system in accordance with yet another embodiment of the present invention, which employs spectrum screen devices.
Figure 11:
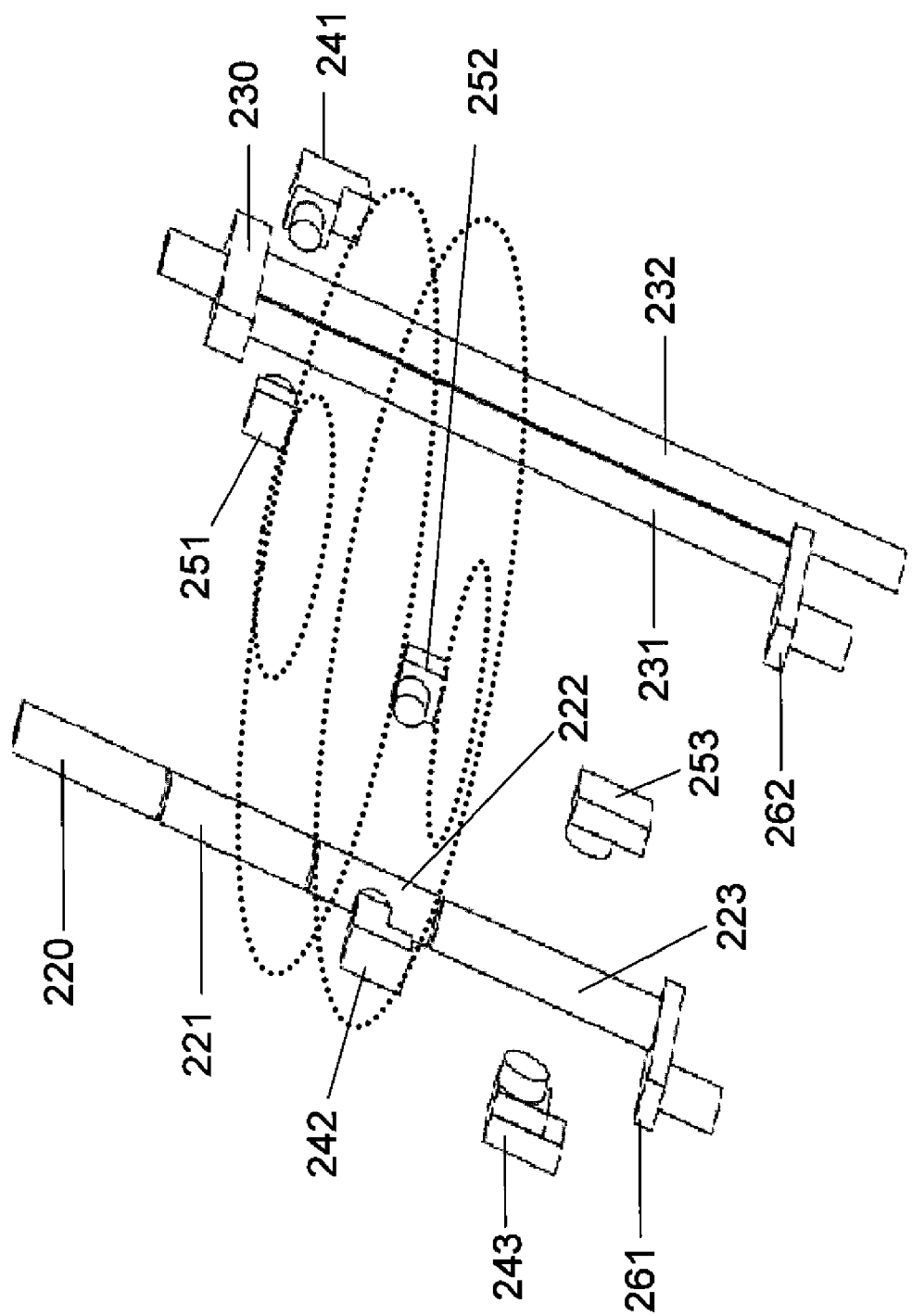
FIG. 11 is a schematic diagram of the high throughput screen system in accordance with yet another embodiment of the present invention.
Figure 12:
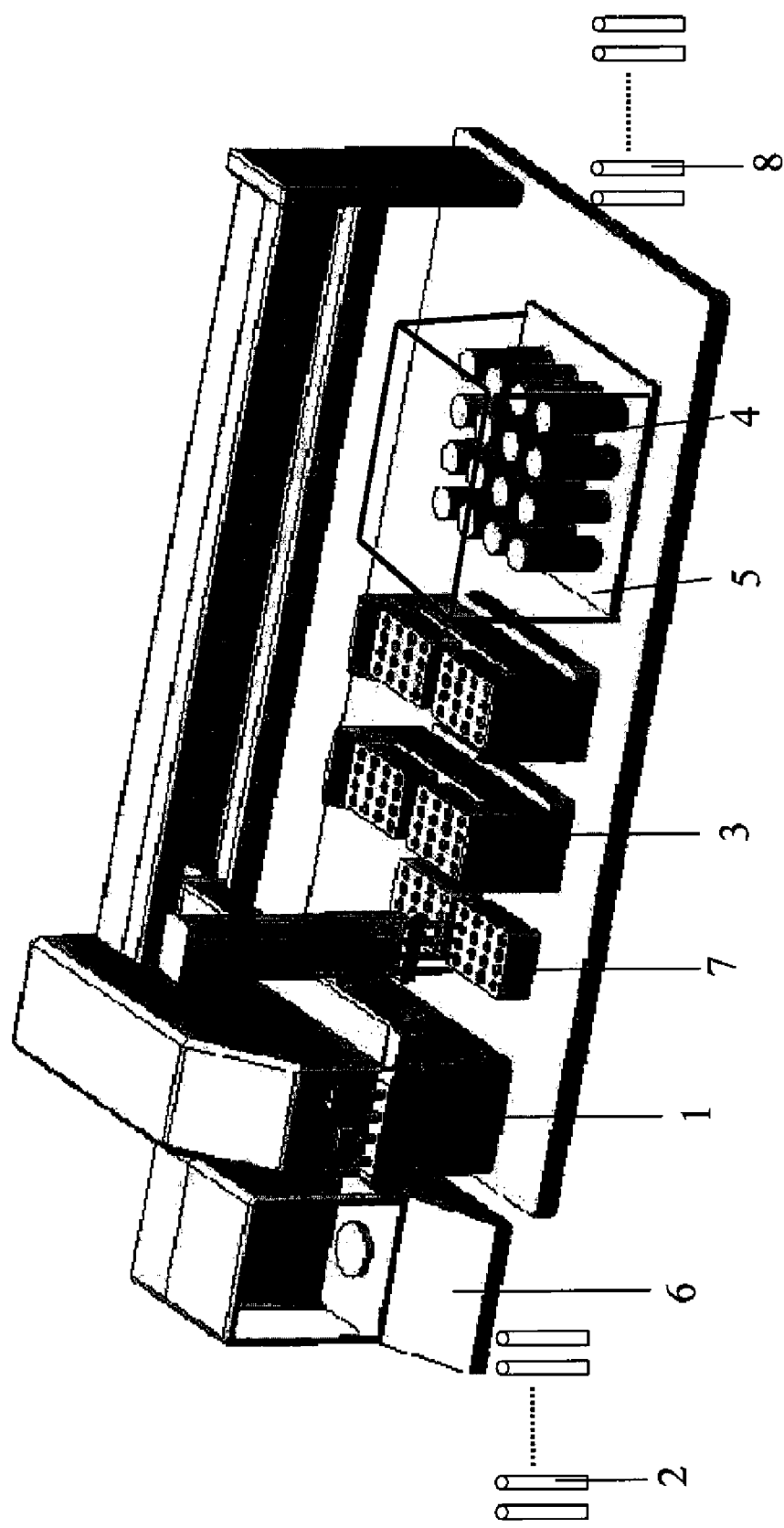
FIG. 12 is a schematic diagram of the high throughput samples preparation system in accordance with one embodiment of the present invention.
Figure 13:
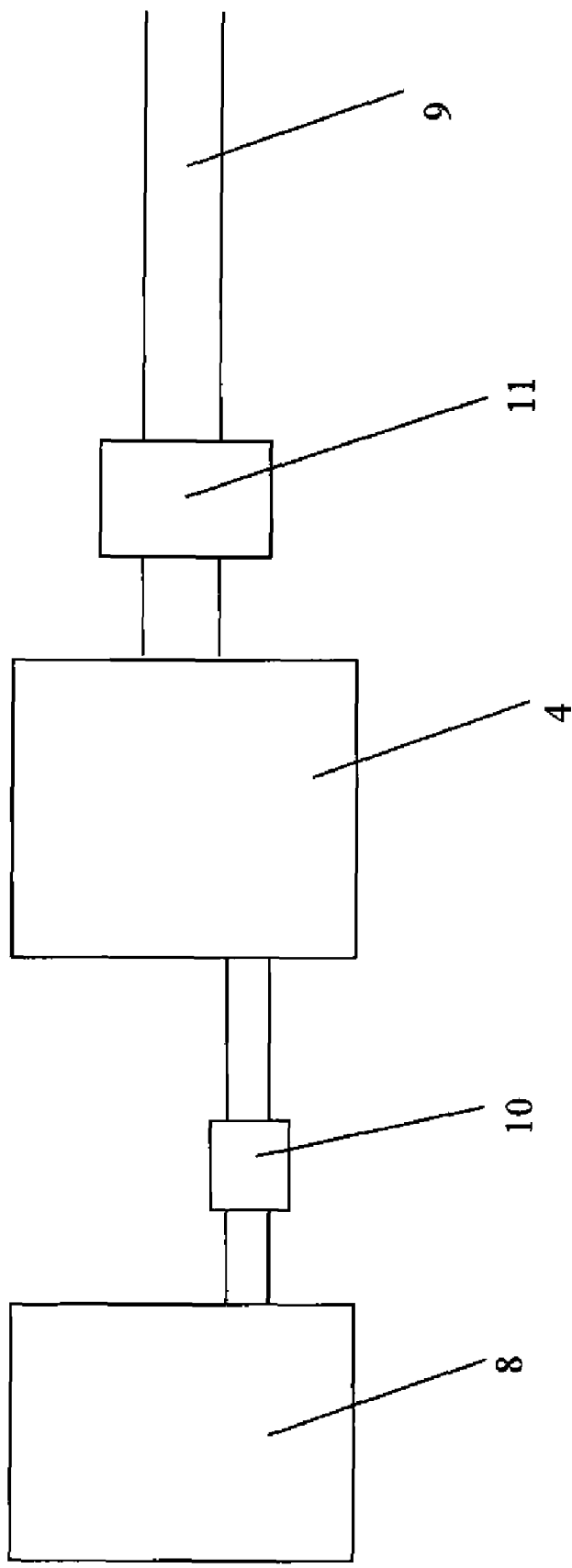
FIG. 13 is a schematic of a connection solution between the high throughput screen system and the high throughput samples preparation system in accordance with one embodiment of the present invention.
Figure 14:
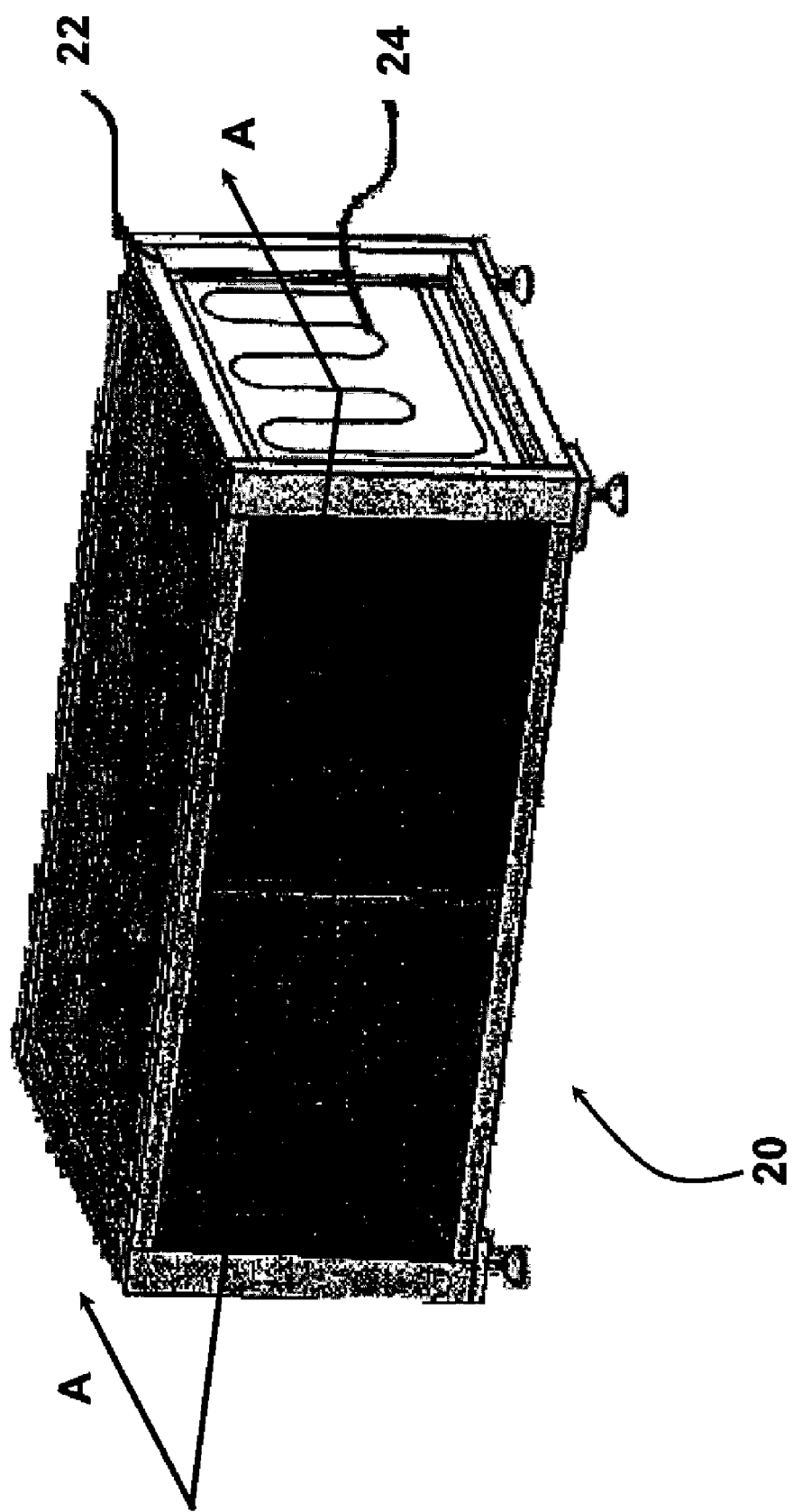
FIG. 14 is a schematic diagram of a temperature control chamber of the present invention, which employs spectrum screen devices.
Figure 15:
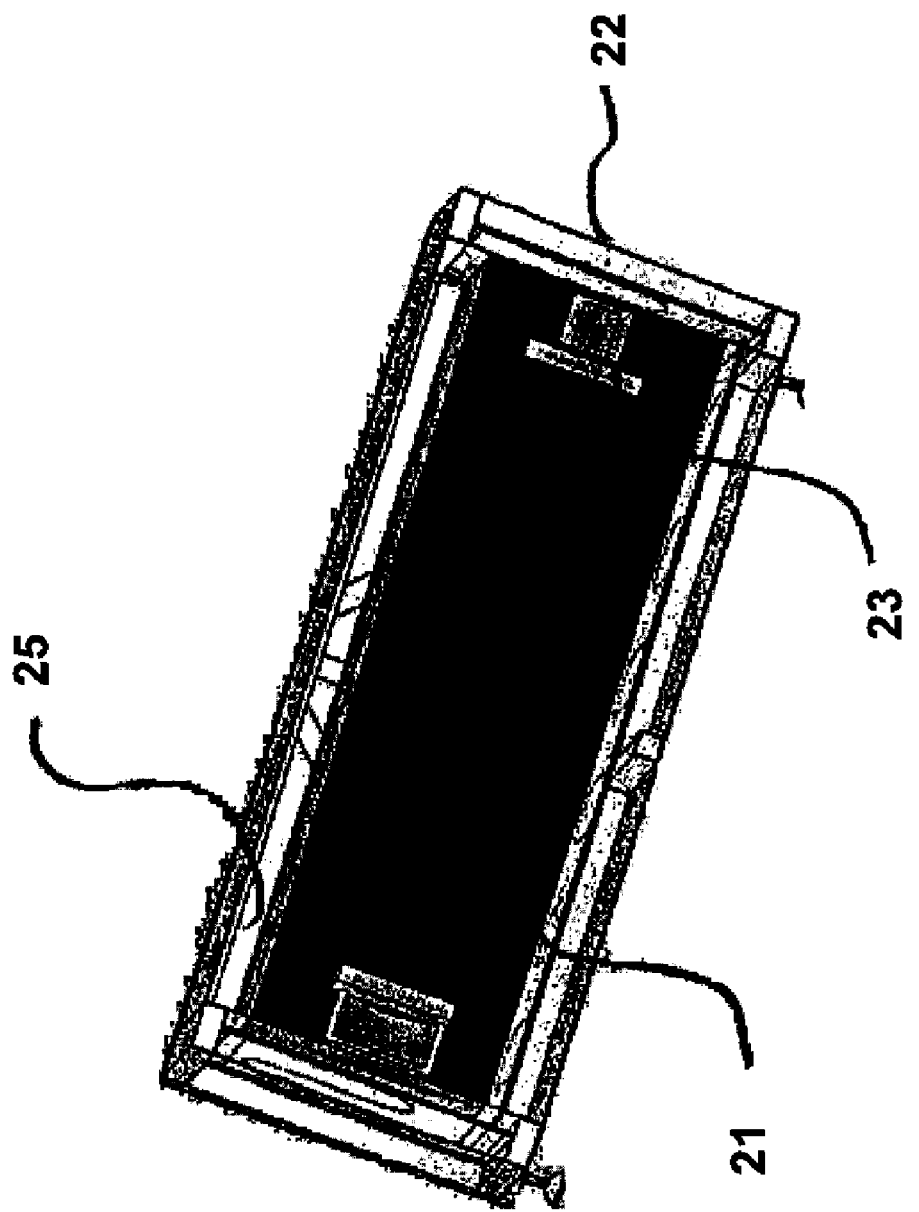
FIG. 15 is a cross section view taken along line A-A of the chamber shown in FIG. 14.
Figure 16:
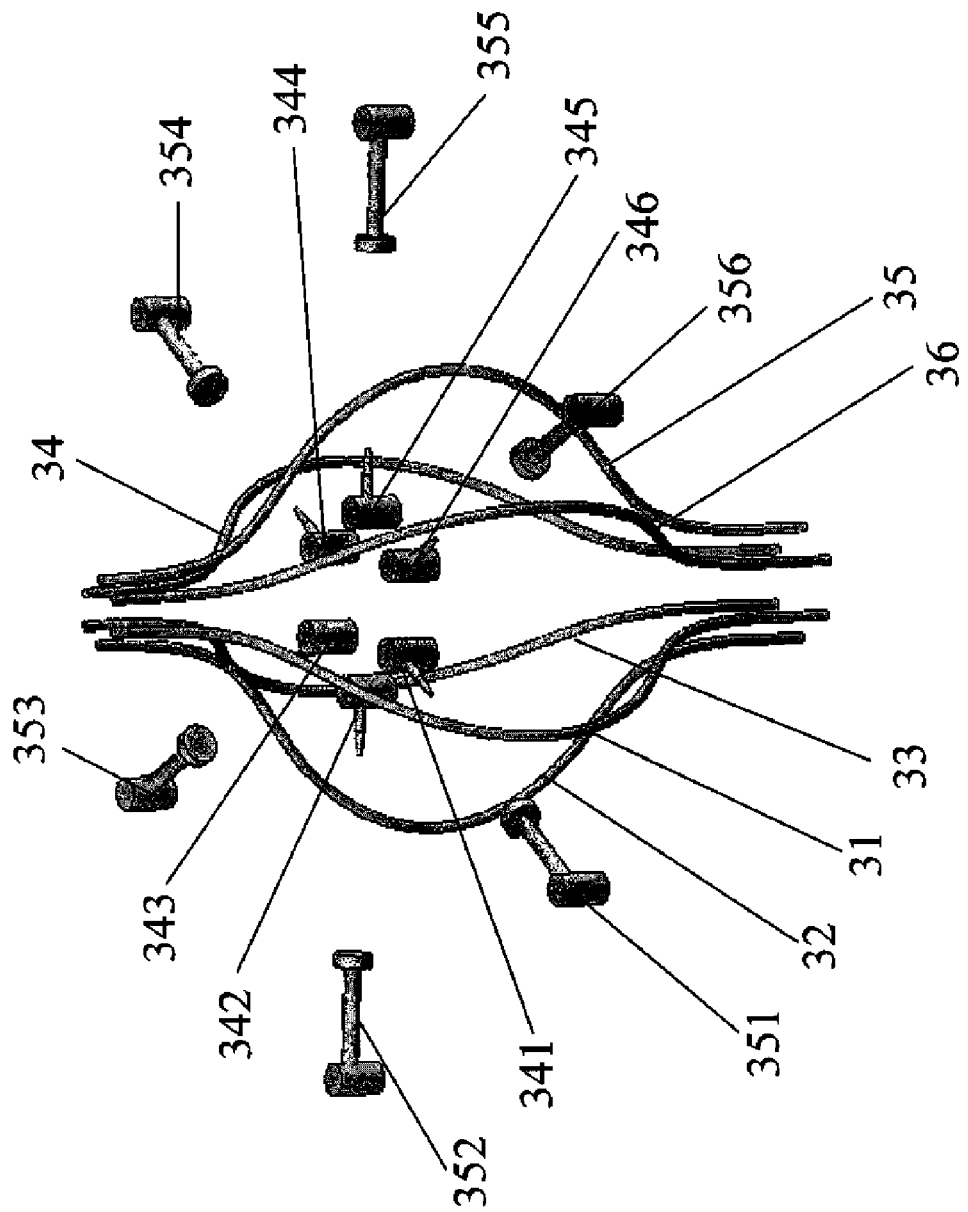
FIG. 16 is a schematic of the high throughput screen system in accordance with yet another embodiment of the present invention.

The following are embodiments of the solution samples preparation and screen by the high throughput preparation system and screen system of the present invention.

1. Embodiment of Preparation and Screen of Polythene Samples

The samples preparation method is high throughput temperature rising elution fractionation, and the screen device of the high throughput screen system is infrared screen device.

Materials: Polythene (Solute), 1,2,4-trichlorobenzene (Solvent and Washing Solvent)

Preparation of Solution Samples:

Putting 8 different polythene samples into 8 corresponding cuvette, respectively, and then using liquid distributor distribute the solvent: 1,2,4-trichlorobenzene to each cuvette to get the solutions with 0.5 mg/ml. Then powering the vibrate heating platform to heat the solutions in the cuvette to 140° C. and vibrating with velocity of 1000 rpm/min. Next, maintaining the temperature and the vibrate velocity for 30 minutes at 140° C., then adding glass beads with 40 mesh into the solutions, and cooling the solutions to 30° C. with temperature decreasing velocity of 1.5° C./hour. Subsequently, filtering and drying the solutions, and putting the rest (glass beads and its attachment) into the columns within a temperature control chamber.

Washing the samples in the column by using a washing solvent, such as 1,2,4-trichlorobenzene and heating the samples with 0.4° C./min temperature rising velocity from 30° C. to 140° C. At the meantime, the solution samples are output to the passages of the screen system to the solution samples.

Screen:

The screen system comprises an infrared screen device, and 8 passages are provided between the radial source and the detector. The wavelength of the ray is 3.41 μm. The radial source and the detector can rotate synchronously with velocity of 12 rpm/min. So, in this case, the interval of two screens for each passage is 5 seconds. The signal intensity recorded by the screen device is firstly transformed into absorptance, and then transformed into concentration of the sample based on the standard curve. Finally, a concentration-temperature curve of samples may be determined for contrasting therebetween?.

2. Embodiment of Preparation and Screen of LLDPE (Linear Low Density Polyethylene) Samples The samples preparation method is high throughput temperature rising elution fractionation, and the screen device of the high throughput screen system is infrared screen device.

Material: LLDPE (Solute), Dimethylbenzene (Solvent and Washing Solvent)

Preparation of the Solution Samples:

Putting 4 different LLDPE samples into 4 corresponding cuvette, respectively, and then using liquid distributor to distribute solvent: dimethylbenzene to each cuvette so as to get the solutions with 6 mg/ml. Then powering the vibrate heating platform to heat the solutions in the cuvette to 130° C. and vibrating with velocity of 800 rpm/min. Next, maintaining the temperature and the vibrate velocity for 30 minutes at 130° C., and then adding glass beads with 60 mesh into the solutions. Next, under nitrogen environment, cooling the solutions to 105° C. with temperature decreasing velocity of 1° C./min, and then with temperature decreasing velocity of 2° C./hour to 25° C. Subsequently, filtering and drying the solutions, and then putting the rest (glass beads and its attachment) into the columns within a temperature control chamber.

In step temperature rising setting, the washing solvent, such as dimethylbenzene is used to wash the samples in the column. The washing temperatures are 47° C., 57° C., 67° C., 77° C., 93° C., 105° C., respectively. The temperature rising velocity is 0.5° C./min. The each step temperature will maintain for 60 minutes. Then, the solution samples are introduced into the passages of the screen system to be screened.

Screen:

The screen system comprises an infrared screen device, and 4 passages are disposed between the radial source and the detector. The wavelength of the ray is 3.41 μm. The radial source and the detector can rotate synchronously with a velocity of 12 rpm/min. So, in this case, the interval of two screens for each passage is 5 seconds. The signal intensity recorded by the screen device firstly is transformed into absorptance, and then into value of concentration of the sample based on standard curve. Finally, a concentration-temperature curve of samples is determined for contrasting therebetween?.

3. Embodiment of Preparation and Screen of Polypropylene Samples

The samples preparation method is the high throughput crystallization analysis fractionation, and the screen device of the high throughput screen system is the infrared screen device.

Materials: Polypropylene (Solute); 1,2,4-trichlorobenzene (Solvent); Nitrogen (Pressure Source)

Preparation of the Solution Samples:

Putting 16 different polypropylene samples into 16 cuvette, respectively, and then using the liquid distributor to distribute solvent: 1,2,4-trichlorobenzene to each cuvette so as to get the solutions with 1 g/L. Then, powering the vibrate heating platform to heat the solutions in the cuvette to 160° C. and vibrating with velocity of 800 rpm/min at the same time. Next, maintaining the temperature and vibrate velocity for 100 minutes at 160° C., and then transiting the solution samples into the columns of a temperature control chamber.

Keeping the temperature of the columns and the solution samples in the column to be 160° C. for 10 minutes. Then cooling them to 30° C. with a velocity of 0.2° C./min, wherein the temperature is held for 15 seconds every 5 minutes during reducing the temperature. Meantime, powering the gas pressure device to drive the solution samples to the passages for screen.

Screen:

The screen system comprises an infrared screen device, which can generate a ray with wavelength of 3.5 μm and has a synchronous angular velocity of 12 rpm/min. So, in this case, the interval of two screens for each passage is 5 seconds. The signal intensity recorded by the screen device is firstly transformed into absorptance, and then into the value of concentration of the sample based on the standard curve. Finally, the concentration-temperature curve of samples is determined for contrasting therebetween.

4. Another Embodiment of Preparation and Screen for Polythene Samples

The samples preparation method is the high throughput crystallization analysis fractionation, and the screen devices of the high throughput screen system are 2 infrared screen devices and a Raman laser screen device.

Materials: Polythene (Solute); 1,2,4-trichlorobenzene (Solvent); Nitrogen (Pressure Source)

Preparation of the Solution Samples:

Putting 32 different polythene samples into 32 cuvette, respectively, and then use the liquid distributor to distribute the solvent: 1,2,4-trichlorobenzene to each cuvette so as to get the solutions with 1 g/L. Then, powering the vibrate heating platform to heat the solutions in the cuvette to 95° C. and vibrating with a velocity of 1000 rpm/min at the same time. Next, maintaining the temperature and vibrating velocity for 100 minutes at 950° C., and then transiting the solution samples into the columns within a temperature control chamber.

Keeping the temperature of the columns and its environment at 95° C. for 10 minutes, and then cooling them down to 25° C. with a velocity of 0.1° C./min, wherein the temperature is held for 15 seconds every 5 minutes during reducing the temperature; Meanwhile, powering the gas pressure device to drive the solution samples to the passages for screening.

Screen:

The screen system comprises 2 infrared screen devices and a Raman laser screen device, which can generate rays with wavelengths of 3.5 µm, 3.6 µm and 7.41 µm, respectively. The screen devices both have the same synchronous angular velocity of 12 rpm/min. So, in this case, the interval of two screens for each passage is 5 seconds. The signal intensity recorded by the screen device is firstly transformed into absorptance, and then into the value of concentration of the sample based on standard curve. Finally, the concentration-temperature curve of samples is determined for contrasting therebetween.

5. Another Embodiment of Preparation and Screen for Polythene Samples

The samples preparation method is the high throughput temperature rising elution fractionation, and the screen device used of the high throughput screen system is the infrared screen device.

Materials: Polythene (Solute); 1,2,4-trichlorobenzene (Solvent, Washing Solvent)

Preparation of Solution Samples

Putting 6 different polythene samples into 6 cuvette, respectively, and then using the liquid distributor to distribute the solvent: 1,2,4-trichlorobenzene to each cuvette so as to get the solutions with 0.5 mg/ml. Then, powering the vibrate heating platform to heat the solutions in the cuvette to 140° C. and vibrating with a velocity of 800 rpm/min. Next, maintaining the temperature and the vibrating velocity for 30 minutes at 140° C., and then adding glass beads with 60 mesh into the solutions. Subsequently, under nitrogen environment, cooling the solutions to 30° C. with a temperature decreasing velocity of 1.5° C./min. Filtering and drying the solutions, and then putting the rest (glass beads and its attachment) into the columns within a temperature control chamber.

Washing the samples in the column by using the washing solvent: 1,2,4-trichlorobenzene and heating the samples with a temperature rising velocity of 0.4° C./min from 30° C. to 140° C. Then delivering the solution samples to the passages of the screen system and beginning the screen process of the solution samples.

Screen:

referring to FIG. 18, the screen system comprises 6 infrared screen devices each comprising radial sources 341, 342, 343, 344, 345, 346 and detectors 351, 352, 353, 354, 355, 356. One infrared screen device is corresponding to one passage 31, 32, 33, 34, 35, 36, and they get a fixed position relationship. The wavelengths of the rays of the radial sources are all 3.41 µm. The signal intensity recorded by the screen device is firstly transformed into absorptance, and then into the value of concentration of the sample based on standard curve. Finally, a concentration-temperature curve of samples is determined for contrasting therebetween.

What is claimed is:

1. A high throughput fluid samples preparation and screen system, comprising
    a plurality of first vessels in which primary sample solutions are prepared;
    a liquid distributor to distribute one or more liquid solvents to the first vessels;
    a vibrating heating platform to vibrate and heat the first vessels; and
    a plurality of second vessels to store the primary sample solutions prepared in the first vessels;
    a temperature control chamber to enclose the second vessels; an inner temperature control element placed within the said temperature control chamber;
    a plurality of passages each connecting to a corresponding second vessel; and
    a plurality of screen devices;
    wherein the screen devices screen the fluid samples flowing through the passages in parallel.

2. The high throughput fluid samples preparation and screen system according to claim 1, further comprising a plurality of third vessels each connected to a corresponding second vessel.

3. The high throughput fluid samples preparation screen system according to claim 1, wherein the screen devices include a spectrum screen device, which comprises a radial source and a detector; and either the radial source or the detector or both are movable.

4. The high throughput fluid samples preparation screen system according to claim 1, wherein the temperature control chamber comprising
    a body enclosing a receiving room for receiving the samples, the body having an outer surface and an inner surface;
    an inner temperature control element and an outer temperature control element provided on the inner surface and the outer surface, respectively; and
    one or more layers of insulating materials provided between the inner surface and the outer surface.

5. A high throughput fluid samples screen method, comprising
    transporting fluid solution samples into respective corresponding passages, wherein portions of the passages are enclosed in a temperature control chamber comprising a body enclosing a receiving room for receiving the samples, the body having an outer surface and an inner surface, an inner temperature control element and an outer temperature control element provided on the inner surface and the outer surface, respectively, and one or more layers of insulating materials provided between the inner surface and the outer surface;
    screening the fluid samples in the passages in parallel as the fluid samples are flowing through portions of the passages enclosed in the temperature control chamber;
    outputting screen data.

6. The high throughput fluid samples screen method according to claim 5, wherein screening is performed using a spectrum screen device, which comprises a radial source and a detector; and parallel screen of the fluid solution samples is accomplished by moving either the radial source or the detector or both.

7. The high throughput fluid samples screen method according to claim 6, wherein signals emitted by the radial source will pass through the fluid solution samples and be received by the detector.

8. The high throughput fluid samples screen method according to claim 5, wherein the fluid solution samples comprise polymer solution samples.

9. The high throughput fluid samples screen method according to claim 5, wherein either the concentration of the fluid solution samples or the structure of the sample dissolved in the solution or both are changing during flowing through the passage.

* * * * *